United States Patent [19]

Gibbs

[11] Patent Number: 5,780,515
[45] Date of Patent: Jul. 14, 1998

[54] BENZOQUINONE AND HYDROQUINONE DERIVATIVES FOR USE AS INSECT FEEDING DETERRENTS

[75] Inventor: Don E. Gibbs, Kansas City, Mo.

[73] Assignee: Rockhurst University, Kansas City, Mo.

[21] Appl. No.: 820,841

[22] Filed: Mar. 20, 1997

Related U.S. Application Data

[60] Provisional application No. 60/013,817 Mar. 21, 1996.

[51] Int. Cl.$^6$ .................. A01N 31/08; A01N 35/00
[52] U.S. Cl. .................. 514/690; 514/731; 514/919; 424/DIG. 10
[58] Field of Search .................. 514/690, 731, 514/919; 424/DIG. 10

[56] References Cited

U.S. PATENT DOCUMENTS

| | | | |
|---|---|---|---|
| 2,769,006 | 10/1956 | Kalberg | 260/270 |
| 4,092,433 | 5/1978 | Crovetti | 424/331 |
| 4,676,985 | 6/1987 | Gould et al. | 424/195.1 |
| 4,855,319 | 8/1989 | Mikolajezak et al. | 514/473 |
| 4,960,791 | 10/1990 | Klocke et al. | 514/468 |
| 5,047,242 | 9/1991 | Klocke et al. | 424/195.1 |
| 5,290,557 | 3/1994 | Mason et al. | 424/410 |

FOREIGN PATENT DOCUMENTS

| | | | |
|---|---|---|---|
| 51-57839 | 5/1976 | Japan | 514/460 |

OTHER PUBLICATIONS

Vlcek et al. C.A. #99:111,441 (1983).
Waldron. C.A.. #69:59166 (1968).
King. Chemicals Evaluated as Insecticides and Repellants at Orlando, Fla. (1954) pp. 1–17, 112, and 194–196.
Rozental, J. M. and Norris, D.M., *Chemosensory Mechanism in American Cockroach Olfaction and Gustation* Nature, vol. 244, pp. 370–371, Aug. 10, 1973.
Norris, D.M., Ferkovich, S.M., Rozental, J.M., Baker, J.E. and Borg, T.K., *Energy Transduction: Inhibition of Cockroach Feeding by Naphthoquinone*, Science, vol. 170, pp. 754–755, Nov., 1970.

*Primary Examiner*—Allen J. Robinson
*Attorney, Agent, or Firm*—Litman, McMahon & Brown, L.L.C.

[57] ABSTRACT

Mono- and di- substituted 1,2 and 1,4 benzoquinones and hydroquinones have been found to have significant feeding deterrent effect with reduced toxicity and irritating effect relative to benzoquinone and hydroquinone. Preferred substituent groups include tert-butyl and tert-amyl.

36 Claims, No Drawings

BENZOQUINONE AND HYDROQUINONE DERIVATIVES FOR USE AS INSECT FEEDING DETERRENTS

This application is a non-provisional application based on Provisional Application Ser. No. 60/013,817 filed Mar. 21, 1996, and entitled INSECT FEEDING DETERRENTS AND THEIR SYNTHESIS.

BACKGROUND OF THE INVENTION

The present invention relates to the identification of compounds which deter feeding by insects and in particular the use of derivatives of the naturally occurring feeding deterrent naphthaquinone.

Heavy use of insecticides presents environmental dangers and promotes the development of resistant insect populations. One alternative to present practices relating to insecticide use involves the application on crops of chemicals which inhibit or deter feeding thereon by insects. Use of naturally occurring feeding deterrents and their derivatives for crop protection is appealing because such compounds do not need to be toxic to work and therefore the additional concerns of toxicity to other animals, and in particular to mammals, are avoided. Folklore and stories of traditional farming practices are replete with references to feeding deterrent or repellent properties of plants. A well known practice involves the placement of hedge apples in the corners of basements or root cellars to repel crickets and other insects, spiders and even some rodents.

Extracts from plants known to exhibit antifeedant activity have been used in compositions developed for commercial utilization. For example, U.S. Pat. No. 5,290,557 to Mason et al. discloses the use of saponin containing extracts of *Yucca schidigera* as an antifeedant to control terrestrial mollusks. Similarly, U.S. Pat. No. 4,676,985 to Gould et al. discloses a process of protecting crops from damage by coating seeds or seedlings with an extract from plants having feeding deterrent activity such as extracts from butterfly milkweed, English ivy, santolina, bergamot, clary and swamp milkweed.

Others have focused on identifying derivatives of naturally occurring insect feeding deterrents which also exhibit feeding deterrent activity and which can be synthesized commercially. U.S. Pat. No. 5,047,242 to Klocke et al. identifies derivatives of azadirachtin which exhibit antifeedant activity. Azadirachtin is a naturally occurring feeding deterrent which can be isolated from the seeds of the neem tree and from the fruits of the chinaberry tree. U.S. Pat. No. 4,960,791 to Klocke et al. identifies antifeedant derivatives of salannin which is a naturally occurring insect antifeedant related to azadirachtin. U.S. Pat. No. 4,855,319 to Mikolajczak et al. discloses use of asimicin as a feeding deterrent. Asimicin is a derivative of tetrahydrofuranoid acetogenins, which are characteristic of the Annonaceae plant family and known feeding deterrents.

As of yet, it does not appear that any of these compositions have achieved wide-spread commercial use or success. The lack of commercial success of such compositions may be due to the relative high cost in obtaining large quantities of the specified plant extracts or in synthesizing the relatively complex chemical derivatives of naturally occurring antifeedants identified to date. Derivatives of naturally occurring feeding deterrents still provide a promising avenue for alternatives to currently available insecticides for use in integrated pest management programs. The compounds should be ecologically sound and non-toxic to mammals. The synthesis of these compounds should be relatively inexpensive and result in the production of relatively stable compounds with the minimal structural components necessary for relatively high activity.

Naphthaquinones, which are found in the heartwood of some trees, are known feeding deterrents. However, naphthaquinones are generally considered toxic to mammals, limiting their commercial applicability.

SUMMARY OF THE INVENTION

The present invention comprises the use of mono- and di-substituted 1,2 and 1,4-benzoquinones and their corresponding hydroquinones or catechols as feeding deterrents. The 1,2 and 1,4 bezoquinones and the corresponding hydroquinones and cathecols identified for use as feeding deterrents generally include the following:

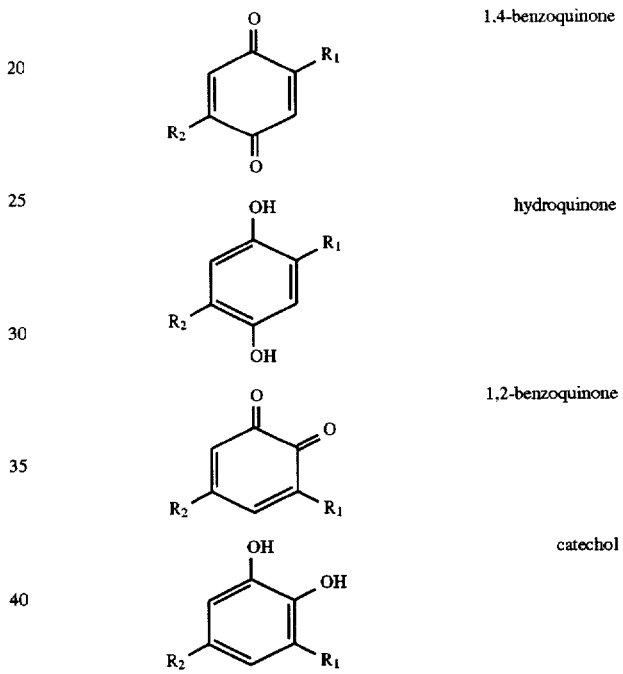

where $R_1$ is H, OH or an alkyl group and $R_2$ is an alkyl group, the alkyl groups preferably comprising $C_4$ and $C_5$ alkyls such as tert-butyl or tert-amyl. For example, a preferred feeding deterrent composition comprises a feeding deterrent effective amount of 2-tert-butyl-1,4-benzoquinone and a suitable carrier.

OBJECTS AND ADVANTAGES OF THE INVENTION

The objects of the present invention include: providing feeding deterrent compositions which are relatively non-toxic and relatively inexpensive to manufacture and to apply at concentrations which are effective at deterring feeding by insects on plants and crop material; providing such compositions which are relatively easy to manufacture; providing such compositions which are effective at deterring feeding even at relatively low concentrations with respect to the plant or crop material to which the compositions are applied; and providing such compositions which are relatively biodegradable.

It is a further object of this invention to identify derivatives of naphthaquinone which function as feeding deterrents but are relatively non-toxic, non-irritating and relatively inexpensive to manufacture and to apply at concentrations which are effective at deterring feeding on plants and crop material.

Other objects and advantages of this invention will become apparent from the following description wherein are set forth, by way of illustration and example, certain embodiments of this invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific composition and functional details disclosed herein are not to be interpreted as limiting, but merely as a basis for the claims and as a representative basis for teaching one skilled in the art to variously employ the present invention in virtually any appropriately detailed structure or composition.

The present invention comprises the use of mono- and di-substituted 1,2 and 1,4-benzoquinones and their corresponding hydroquinones and catechols as feeding deterrents. The 1,2 and 1,4 bezoquinones, hydroquinones and catechols which can be used as feeding deterrents generally include the following:

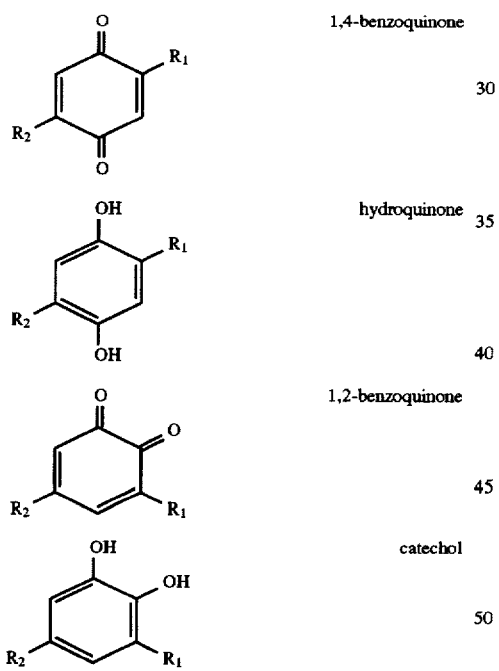

where $R_1$ is H, OH or an alkyl group and $R_2$ is an alkyl group, the alkyl groups preferably comprising $C_4$ and $C_5$ alkyls such as tert- butyl or tert-amyl. For example, a preferred feeding deterrent composition comprises a feeding deterrent effective amount of 2-tert-butyl-1,4-benzoquinone and a suitable carrier. Other preferred compositions include a feeding deterrent effective amount of 2,5-di-tert-butyl-1, 4-benzoquinone; 3,5-di-tert-butyl- 1,2-benzoquinone; 2,5-di-tert-amyl-1,4-benzoquinone, 3,5-di-tert-amyl-1,2-benzoquinone, 2-tert-butyl-5-hydroxy-1,4-benzoquinone, 3-tert-butyl-5-hydroxy-1,2-benzoquinone, 3-hydroxy-5-tert-butyl-1,2-benzoquinone, 2-tert-amyl-5-hydroxy-1,4-benzoquinone, 3-tert-amyl-5-hydroxy-1,2-benzoquinone, and 3-hydroxy-5-tert-amyl-1,2-benzoquinone and the corresponding hydroquinones and catechols.

It has been postulated that an insect food sensory protein has amino and thiol groups with rigid steric requirements for binding via conjugate addition/redox reaction or imine/heterocycle formation with active compounds. It has been reported that naphthaquinone reacts with sulphydryl groups of a food sensory protein on an insects antennae to deter feeding. Benzoquinone, hydroquinone and catechol have not been reported as insect feeding deterrents but are known to be toxic and irritants to animals. It is postulated that benzoquinones, hydroquinones and catechols react with the insect food sensory protein to deter feeding in a manner similar to that of naphthaquinone and generally as follows:

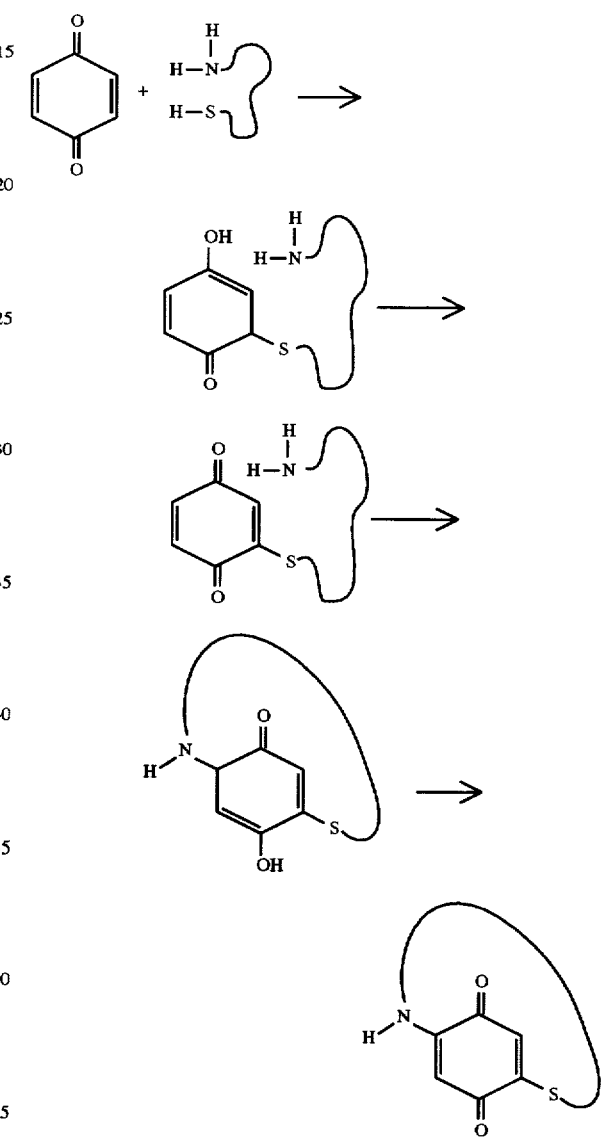

It should be noted that hydroquinones and cathecols interconvert to benzoquinones under biological/environmental conditions.

It has been discovered that mono- and di-substituted 1,2 and 1,4 benzoquinones, hydroquinones and catechols, wherein at least one of the substituent groups comprises an alkyl, exhibit a feeding deterrent effect often with reduced or insignificant toxicity or irritating effect on animals. Preferred alkyl substituent groups include $C_4$–$C_5$ alkyls such as tert-butyl and tert-amyl groups. 2-tert-butyl-1,4- benzoquinone is commercially available and is used in cosmetics which would indicate low toxicity and irritating effect to mammals.

Methods of synthesizing mono- and di-substituted 1,2 benzoquinones and catechols and mono- and di-substituted 1,4 benzoquinones and hydroquinones are well known in the art. Hydroquinone, catechol, 1,2-benzoquinone and 1,4- or p-benzoquinone are commercially available. Alkyl groups may be added to hydroquinone and catechol through a Friedel-Crafts reaction with the corresponding alcohol. For example mono-tert-butyl-hydroquinone is synthesized from a Friedel-Crafts reaction of one mole hydroquinone with one mole of tert-butyl alcohol, and di-tert-butyl-hydroquinone is synthesized from a Friedel-Crafts reaction of one mole hydroquinone with two moles of tert-butyl alcohol. The hydroquinone or catechol is converted to the corresponding benzoquinone through oxidation with sodium hypochlorite in stoichiometric amounts.

Reaction of a mono-alkyl-hydroquinone or catechol with sodium hypochlorite in excess of the stoichiometric amount will result in the addition of a hydroxyl group to the resultant benzoquinone, such as 2-tert-butyl-5-hydroxy-1,4-benzoquinone. A mono-alkyl-hydroquinone or catechol with a hydroxyl substituent group may be produced by reduction of the corresponding benzoquinone with sodium borohydride or with hydrogen gas and a platinum catalyst. For example, 2-tert-butyl-5-hydroxy-hydroquinone may be produced from the reduction of 2-tert-butyl-5-hydroxy-1,4-benzoquinone.

Benzoquinones, hydroquinones and catechols are generally solids at ambient conditions for application of feeding deterrents on plant or crop material. Benzoquinone and alkyl substituted benzoquinones are generally insoluble in water. The addition of a hydroxyl group as a substituent group to a benzoquinone increases its solubility in water. Although hydroquinone and catechol are generally soluble in water, the addition of alkyl groups thereto reduces the solubility of these compounds. However, the solubility of these compounds in water can be increased through the addition of a hydroxyl group as a substituent group.

Although the carrier utilized in the tests discussed below comprises an organic solvent, ethyl acetate, it is not intended that the present application be limited to any particular carrier and it is foreseen that the active compounds of the present invention could be applied utilizing a wide range of carriers or formulations now known or subsequently developed. It is foreseen that the active compounds could be applied to crop or plant material in liquid or solid compositions or in solid suspensions or without a carrier. The hydroxy substituted benzoquinones, hydroquinone and catechols are more readily soluble in water which is a preferred liquid carrier. It is also foreseen that a wide range of additives could also be utilized in the feeding deterrent compositions to facilitate application, to stabilize the composition and for other reasons well known in the art.

The feeding deterrent effect of various mono- and di-substituted benzoquinones and hydroquinones was evaluated through choice tests and weight gain tests on third to fifth instar larvae of *Tenebrio molitor* (mealworm, flour beetle larvae), third-instar larvae of *Manduca sexta* (tomato hornworm) and with juvenile *Acheta domestica* (common cricket). Screening for toxicity was done with larvae of *Artemia salina* (brine shrimp). Insect cultures and food were obtained from Carolina Biological Supply Co., Burlington, N.C.

Test compounds in an ethyl acetate solution were applied by pipet to a weighed food sample and the mixture was stirred thoroughly in glass or stainless steel trays. References to concentrations of test compounds are reported as parts per million (ppm) by weight of pure test compound relative to the weight of the food sample. Treated food was left in open trays for twenty-four hours before insects were introduced. Controls of food treated with ethyl acetate were prepared according to the same procedure. Insect trials with food treated by solvent only (control) versus food with no treatment showed no evidence of solvent residue effects.

For the choice tests, forty *T. molitor* larvae were placed on a tray having a first and a second supply of bran meal (60 grams each) on opposite ends thereof. The larvae were placed in groups on each food supply. The first supply of bran meal was treated with a solution of the test compound and the carrier, ethyl acetate as noted above. The test compound was applied to the food at a concentration of 800 parts per million (weight of test compound to weight of bran meal). The second supply of bran meal was treated with an equivalent amount of ethyl acetate as noted above. The second supply of food may be referred to as untreated food. The first and second supplies of bran meal were maintained in separate areas in the container separated by a screen across which the larvae could traverse. The trays were covered with lids that allowed air flow.

The number of larvae at each end were counted at 7-day intervals. The percentage of larvae on the control or untreated food is indicative of the feeding deterrent effect of the test compound.

Growth tests of *T. molitor* were done by putting 40 larvae on 120 grams of treated and untreated food and periodically weighing the insects. Weight gain for insects on treated food is reported as a percentage of the weight gain for insects on the control or untreated food. The percentage of dead insects was also recorded. Typical mortality for the controls were 0% at 7 days, 3% at 14 days and 5% at 21 days.

Feeding tests with *M. sexta* were made by putting one insect in a covered dish containing two 3.5 cm culture dishes. The food was prepared according to the formula of Yamamoto reported in Yamamoto, R. T., *J. Econ. Entom.* 1969, 62, 1427. One dish contained 5.0 grams of food treated with the test compound and solvent and the other contained 5.0 grams of food treated with solvent only. Each dish was weighed at 1-day intervals for one week.

Feeding tests with *A. domestica* were done using 30.0 grams of food in 5 cm culture dishes (one experimental and one control) in covered trays with two insects per tray. Dishes were weighed at 7 day intervals. Feeding tests were also conducted with azadirachtin, the principle active component of neem oil, and rotenone, the insecticide in Derris root, both natural products with well-documented insect feeding deterrence. Both of these reference compounds were obtained from Sigma Chemical Co., St. Louis, Mo. Results of feeding tests are shown in Table 2.

Table 1 provides results from the choice tests with *T. molitor*. The table includes an indication of the percentage of insect larvae in the area of the untreated food (i.e. the percentage which preferred the untreated food). The reference to days with each percentage indicates the number of days from the beginning of the test on which the observation was made. The test compounds utilized were (1) p-benzoquinone; (2) hydroquinone; (3) 2-tert-butyl-1,4-benzoquinone; (4) 2-tert-butyl-1,4-hydroquinone; (5) 2,5-di-tert-amyl-1,4-benzoquinone; (6) 2,5-di-tert-amyl-1,4-hydroquinone; (7) 2,5-di-tert-butyl-1,4-benzoquinone; and (8) 2,5-di-tert-butyl-1,4-hydroquinone.

TABLE 1

Choice Tests for Benzoquinones and Hydroquiones

| Test Compound | Conc. (ppm) | % Insects on untreated food (days) | | | | | | |
|---|---|---|---|---|---|---|---|---|
| | | (7) | (14) | (21) | (28) | (35) | (42) | (49) |
| p-benzoquinone | 800 | 68 | 59 | 71 | 76 | 78 | 81 | 71 |
| hydroquinone | 800 | 82 | 55 | 74 | 54 | NA | 81 | 63 |
| 2-tert-butyl-1,4-benzoquinone | 800 | 86 | 91 | 91 | 92 | 77 | 83 | 63 |
| 2-tert-butyl-1,4-hydroquinone | 800 | 76 | 68 | 68 | 26 | NA | 77 | 71 |
| 2,5-di-tert-amyl-1,4-benzoquinone | 800 | 95 | 84 | 70 | 64 | 92 | 69 | 89 |
| 2,5-di-tert-amyl-1,4-hydroquinone | 800 | 82 | 85 | 92 | 76 | 79 | 76 | 70 |
| 2,5-di-tert-butyl-1,4-benzoquinone | 800 | 76 | 72 | 81 | 61 | 51 | 39 | 61 |
| 2,5-di-tert-butyl-1,4-hydroquinone | 800 | 60 | 89 | 92 | 54 | 51 | 59 | 62 |

NA indicates that data was not available

TABLE 2

Weight Change Relative to Control or Reference

| Test Compound | Conc. (ppm) | % Wt. change relative to control/reference after 7 days |
|---|---|---|
| 2-tert-butyl-1,4-hydroquinone | 400 | 59 relative to control |
| Azadirachtin | 50 | 100 relative to control |
| 2-tert-butyl-1,4-benzoquinone | 400 | 43 relative to rotenone at 400 ppm |
| 3,5-di-tert-butyl-1,2-benzoquinone | 400 | 5 relative to control |

For the data in Table 2, the compounds 2-tert-butyl-1,4-benzoquinone and rotenone were tested on *A. domestica* and all others were tested on *M. sexta*.

Both the choice tests and weight change tests indicate feeding deterrent effect or antifeedant activity to varying degrees for the bezoquinones and hydroquinones listed in Tables 1 and 2 at the concentrations specified.

For toxicity screening, a suspension of the test compound was prepared by sonicating a mixture of 40 mg of test compound and 250 ml of artificial sea water. One hundred *A. salina* larvae (brine shrimp) were introduced in the aerated mixture and the number of dead organisms was counted periodically. Lapachol, which is isolated from Lapacho heartwood, was used to represent a naturally occurring quinone. A control of artificial seawater alone was also utilized. Table 3, provides results from toxicity screening of selected compounds.

TABLE 3

Toxicity Screening

| Compound | Number Dead/100 | |
|---|---|---|
| | 4 days | 7 days |
| 2-tert-butyl-1,4-benzoquinone | 28 | 47 |
| 2,5-di-tert-butyl-1,4-benzoquinone | 87 | 100 |

TABLE 3-continued

Toxicity Screening

| Compound | Number Dead/100 | |
|---|---|---|
| | 4 days | 7 days |
| lapachol | 48 | 100 |
| control | 6 | 31 |

Although the 2,5-di-tert-butyl-1,4-benzoquinone showed relatively high toxicity to brine shrimp, brine shrimp are relatively sensitive and the associated toxicity to animals may be relatively small and further research as to the toxicity is necessary. The mono-tert-butyl-1,4-benzoquinone showed relatively low toxicity particularly in view of the sensitivity of brine shrimp.

Although the active compounds disclosed herein are discussed for use in deterring insects from feeding of plant and crop material and the like it is foreseen that the active compounds may also exhibit a feeding deterrent effect on terrestrial mollusks, nematodes or other related creatures which feed on plant and crop material.

Further it is foreseen that various chemical equivalents or isomers of the specified active compounds may also provide a feeding deterrent effect.

It is to be understood that while certain forms of the present invention have been illustrated and described herein, it is not to be limited to the specific forms or compositions, equivalents or isomers described and shown.

What is claimed and desired to be secured by Letters Patent is as follows:

1. A method of deterring the feeding activity of insects on plant and crop material comprising the step of:

(a) applying to said material an insect feeding deterrent effective amount of an active compound of the formula:

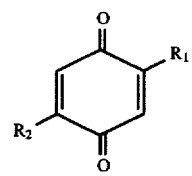

where $R_1$ is a $C_4$ or $C_5$ alkyl group and $R_2$ is H, OH or a $C_4$ or $C_5$ alkyl group.

2. The method as in claim 1 wherein:

(a) $R_1$ is a tertiary alkyl group and $R_2$ is H, OH or a tertiary alkyl group.

3. The method as in claim 1 wherein:

(a) said active compound comprises 2-tert-butyl-1,4-benzoquinone.

4. The method as in claim 1 wherein:

(a) said active compound comprises 2-5-di-tert-butyl-1,4-benzoquinone.

5. The method as in claim 1 wherein:

(a) said active compound comprises 2-tert-butyl-5-hydroxy-1,4-benzoquinone.

6. The method as in claim 1 wherein:

(a) said active compound comprises 2-tert-amyl-1,4-benzoquinone.

7. The method as in claim 1 wherein:

(a) said active compound comprises 2-5-di-tert-amyl-1,4-benzoquinone.

8. The method as in claim 1 wherein:

(a) said active compound comprises 2-tert-amyl-5-hydroxy-1,4-benzoquinone.

9. A method of deterring the feeding activity of insects on plant and crop material comprising the step of:

(a) applying to said material an insect feeding deterrent effective amount of an active compound of the formula:

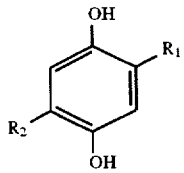

where $R_1$ is a $C_4$ or $C_5$ alkyl group and $R_2$ is H, OH or a $C_4$ or $C_5$ alkyl group.

10. The method as in claim 9 wherein:
(a) $R_1$ is a tertiary alkyl group and $R_2$ is H, OH or a tertiary alkyl group.

11. The method as in claim 9 wherein:
(a) said active compound comprises 2-tert-butyl-hydroquinone.

12. The method as in claim 9 wherein:
(a) said active compound comprises 2-5-di-tert-butyl-hydroquinone.

13. The method as in claim 9 wherein:
(a) said active compound comprises 2-tert-butyl-5-hydroxy-hydroquinone.

14. The method as in claim 9 wherein:
(a) said active compound comprises 2-tert-amyl-1,4-hydroquinone.

15. The method as in claim 9 wherein:
(a) said active compound comprises 2-5-di-tert-amyl-hydroquinone.

16. The method as in claim 9 wherein:
(a) said active compound comprises 2-tert-amyl-5-hydroxy-hydroquinone.

17. A method of deterring the feeding activity of insects on plant and crop material comprising the step of:

(a) applying to said material an insect feeding deterrent effective amount of an active compound of the formula:

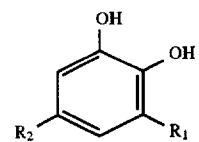

where $R_1$ is a $C_4$ or $C_5$ alkyl group and $R_2$ is H, OH or a $C_4$ or $C_5$ alkyl group.

18. The method as in claim 17 wherein:
(a) $R_1$ is a tertiary alkyl group and $R_2$ is H, OH or a tertiary alkyl group.

19. The method as in claim 17 wherein:
(a) said active compound comprises tert-butyl-1,2-benzoquinone.

20. The method as in claim 17 wherein:
(a) said active compound comprises 3-5-di-tert-butyl-1,2-benzoquinone.

21. The method as in claim 17 wherein:
(a) said active compound comprises 3-tert-butyl-5-hydroxy-1,2-benzoquinone.

22. The method as in claim 17 wherein:
(a) said active compound comprises 3-hydroxy-5-tert-butyl-1,2-benzoquinone.

23. The method as in claim 17 wherein:
(a) said active compound comprises tert-amyl-1,2-benzoquinone.

24. The method as in claim 17 wherein:
(a) said active compound comprises 3-5-di-tert-amyl-1,2-benzoquinone.

25. The method as in claim 17 wherein:
(a) said active compound comprises 3-tert-amyl-5-hydroxy-1,2-benzoquinone.

26. The method as in claim 17 wherein:
(a) said active compound comprises 3-hydroxy-5-tert-amyl-1,2-benzoquinone.

27. A method of deterring the feeding activity of insects on plant and crop material comprising the step of:

(a) applying to said material an insect feeding deterrent effective amount of an active compound of the formula:

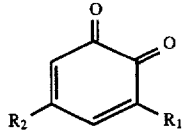

where $R_1$ is a $C_4$ or $C_5$ alkyl group and $R_2$ is H, OH or a $C_4$ or $C_5$ alkyl group.

28. The method as in claim 27 wherein:
(a) $R_1$ is a tertiary alkyl group and $R_2$ is H, OH or a tertiary alkyl group.

29. The method as in claim 27 wherein:
(a) said active compound comprises tert-butyl-catechol.

30. The method as in claim 27 wherein:
(a) said active compound comprises 3-5-di-tert-butyl-catechol.

31. The method as in claim 27 wherein:
(a) said active compound comprises 3-tert-butyl-5-hydroxy-catechol.

32. The method as in claim 27 wherein:
(a) said active compound comprises 3-hydroxy-5-tert-butyl-catechol.

33. The method as in claim 27 wherein:
(a) said active compound comprises tert-amyl-catechol.

34. The method as in claim 27 wherein:
(a) said active compound comprises 3-5-di-tert-amyl-catechol.

35. The method as in claim 27 wherein:
(a) said active compound comprises 3-tert-amyl-5-hydroxy-catechol.

36. The method as in claim 27 wherein:
(a) said active compound comprises 3-hydroxy-5-tert-amyl-catechol.

* * * * *